(12) United States Patent
Annable et al.

(10) Patent No.: US 6,465,244 B1
(45) Date of Patent: Oct. 15, 2002

(54) CONTROLLED ATMOSPHERE EQUIPMENT

(75) Inventors: Michael John Annable; Evan Jonathan Kitsell, both of Keighley; Julian Stuart Walton, Bradford, all of (GB)

(73) Assignee: Don Whitley Scientific Limited, Shipley (GB)

( * ) Notice: Subject to any disclaimer, the term of this patent is extended or adjusted under 35 U.S.C. 154(b) by 0 days.

(21) Appl. No.: 09/403,566

(22) PCT Filed: Apr. 24, 1998

(86) PCT No.: PCT/GB98/01047
§ 371 (c)(1),
(2), (4) Date: Oct. 25, 1999

(87) PCT Pub. No.: WO98/48980
PCT Pub. Date: Nov. 5, 1998

(30) Foreign Application Priority Data

Apr. 25, 1997 (GB) ............................................. 9708368

(51) Int. Cl.[7] .............................................. C12M 1/00
(52) U.S. Cl. .................... 435/303.2; 435/801; 435/809; 119/311; 600/21; 600/22
(58) Field of Search ........................... 435/303.1, 303.2, 435/801, 809; 600/21, 22; 119/311

(56) References Cited

U.S. PATENT DOCUMENTS 5,219,215 A * 6/1993 Akagawa et al. .............. 312/1

FOREIGN PATENT DOCUMENTS

| EP | 0411794 A1 | * | 2/1991 |
| WO | 96/11092 | * | 4/1996 |

* cited by examiner

Primary Examiner—David A. Redding
(74) Attorney, Agent, or Firm—Chapman and Cutler

(57) ABSTRACT

Controlled atmosphere entry/exit lock unit (10) for association with a controlled atmosphere cabinet (80), the lock unit (10) having two controlled access means (13; 30) both usually operable alternatively for sealing and communicating, one (30) relative to said cabinet (80) and the other (13) relative to outside, the lock unit further having atmosphere control means (70–78) operable for achieving internal atmosphere conditions compatible with what may be prescribed for said cabinet (80), the one access means having movable door means (30) and related powered actuation means (50; 30A, B) including for sealing relative to access with said cabinet (80).

19 Claims, 4 Drawing Sheets

CONTROLLED ATMOSPHERE EQUIPMENT

Figure 1:
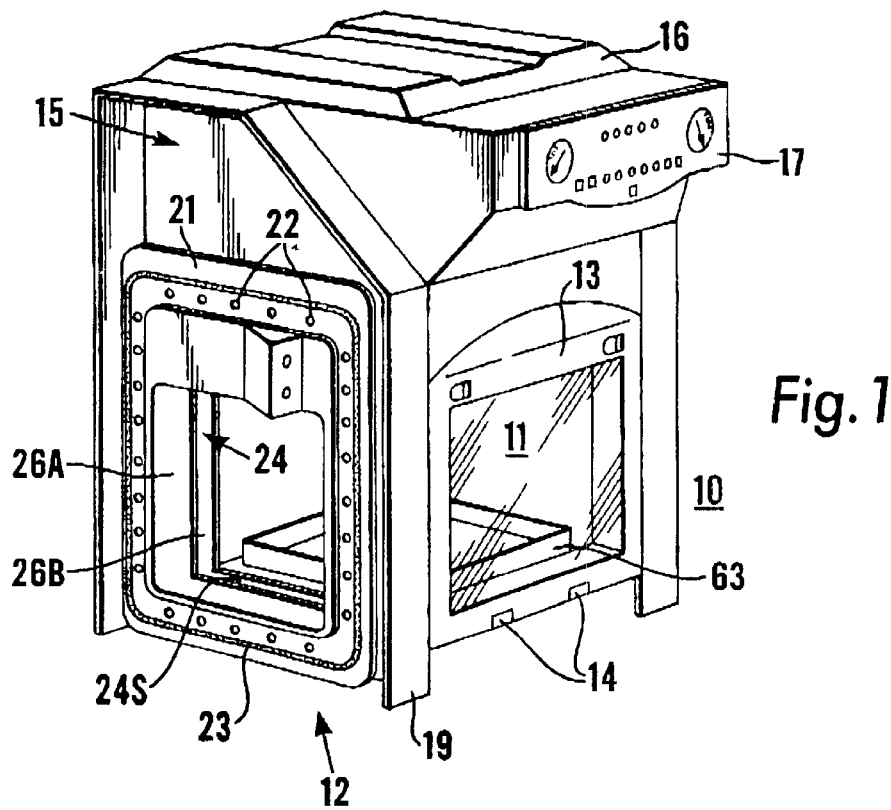

This invention relates to controlled atmosphere equipment, such as, but not limited to, cabinets as used extesrively in microbiology laboratories, and whether of anaerobic or other prescribed or prescribable atmosphere type.

We are particularly interested in entry/exit lock provisions for loading and unloading purposes, typically as units associatable with such cabinet(s) and thus intendedly also having prescribable maintained internal atmosphere different from ambient. Suitable such lock unit(s) require two controlled access means, both operable alternately for sealing and communicating one relative to the cabinet and referred co herein as inner access means, and the other relative to the outside world and referred to herein as outer access means.; also atmosphere control means operable for achieving internal atmosphere conditions acceptable relative to, normally substantially matching, what is prescribed for the cabinet.

Some aspects of this invention have particular relevance to such inner access means, typically of a powered nature, preferably with one or more of actuator means operable manually from within an associated cabinet and/or from outside the lock unit ead/or cabinet; and/or inter-relation of powering for movement of inner door means and of sealing means; and/or inter-relation of holding door means against movement in certain circumstances, such as any failure or deficieney as to powering and/or internal atmosphere and/or sealing conditions; and/or movement and sealing both being by pressuriged fluid means, conveniently gas of or involved in prescribed atmosphere.

Suitable inner door means can be of a sliding nature, say, and advantageously, with up-and-down movnement for open (up) and closed (down) states. Powering of such sliding movement can, with advantage, be by gas from a compressed sras cylinder. Sealing may be by resilient, feasibly flexible tubular, strip along or adjacent to edges of the door as such on one side, say with operation by inflatable bellows type means on the other side of the door. Closing (lower as above) edge of the door pref erably displaces resilient abutmant.

Preferred sliding door embodiments of inner access provisions are well-suited to implementation in double-skinned cavity wall structures, whether to either or both of opposite sides of a generally cuboid casing, or to a side opposite provision of outer access means, or both or all. Indeed, a considerable degree of modular type of standardisation may be provided by way of options as to parts of such wall structures being apertured or not.

Our PCT application No PCT/GB95/02369. (published WO 96/11092) relates, inter alia, to a generally modular cabinet system, of which one module can be an entry/exit lock unit able to communicate with cabinets to either side. thus suited to using ebodiments of this invention.

Other aspects of this invention have relevance to loading and unloading aids, including stackable trays for sample stacks above storage for ancillary materiaes etc; and/or interlock provisions for the outer access means, such as preventing opening of its inner and/or outer door means, even manually, in certain aberrant system conditions, whether of internal atmosphere or door moving/sealing power supply or other operational fault.

Figure 2:
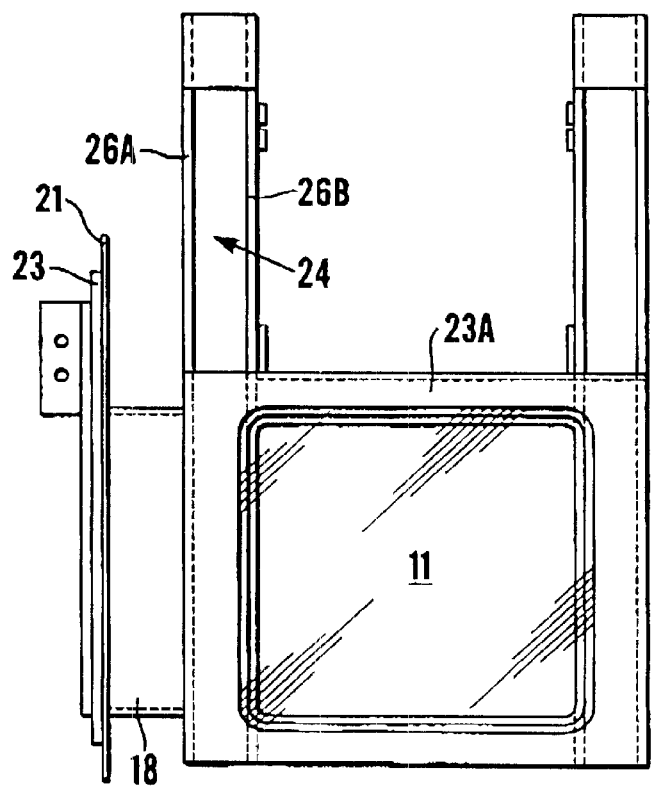
Figure 3A:
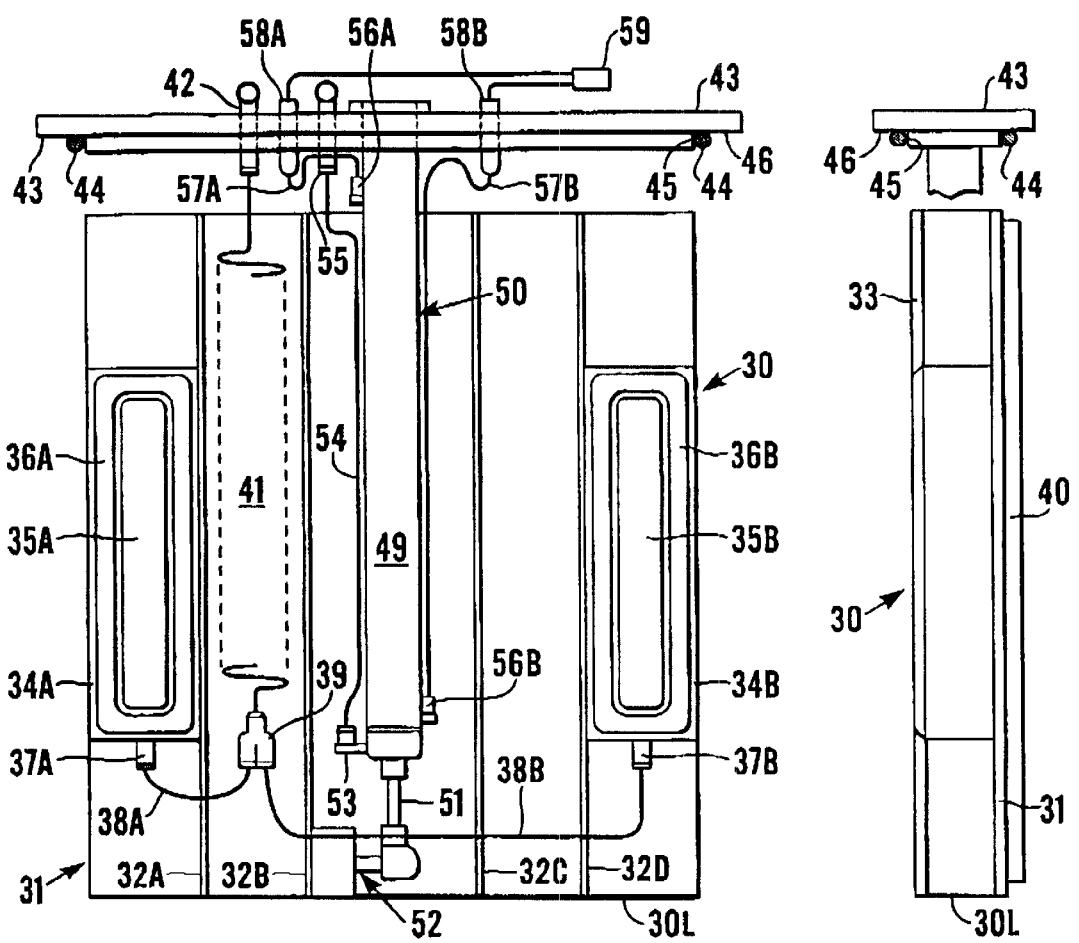
Figure 3B:
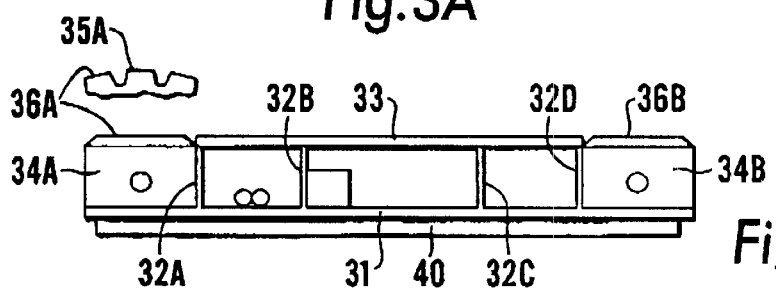
Figure 3C:
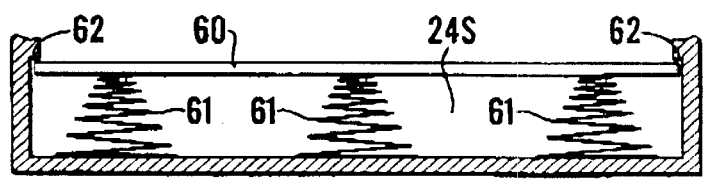
Figures 4A, 4B:
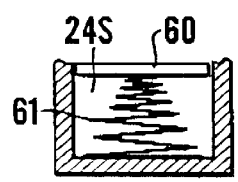
Figure 5A:
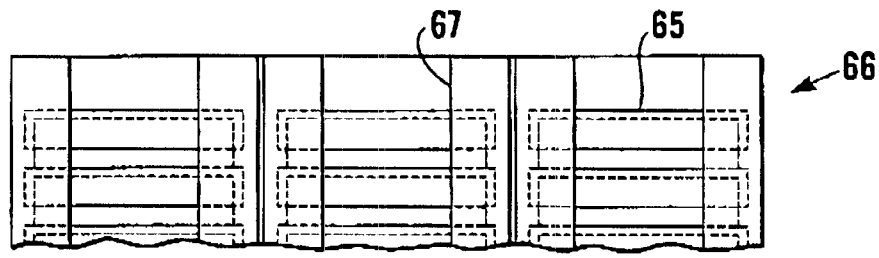
Figure 5B:
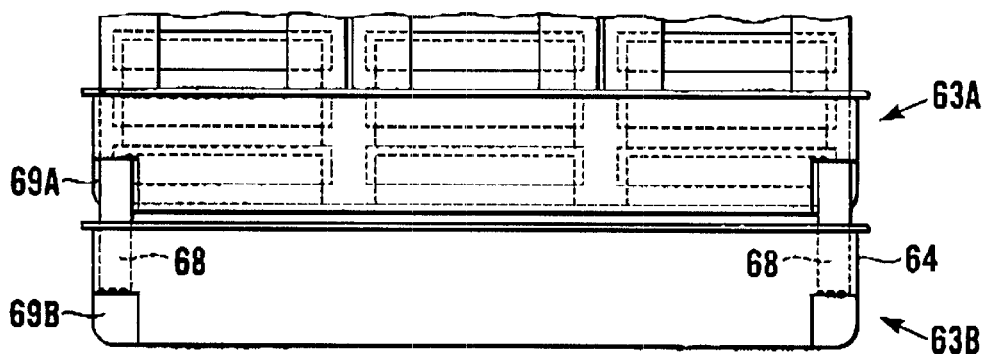
Figure 6A:
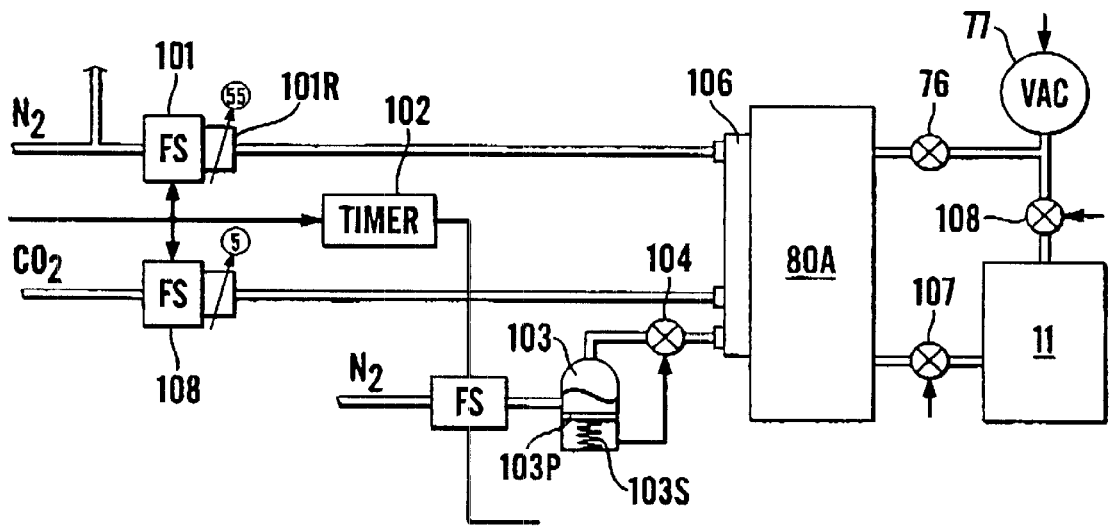
Figure 6:
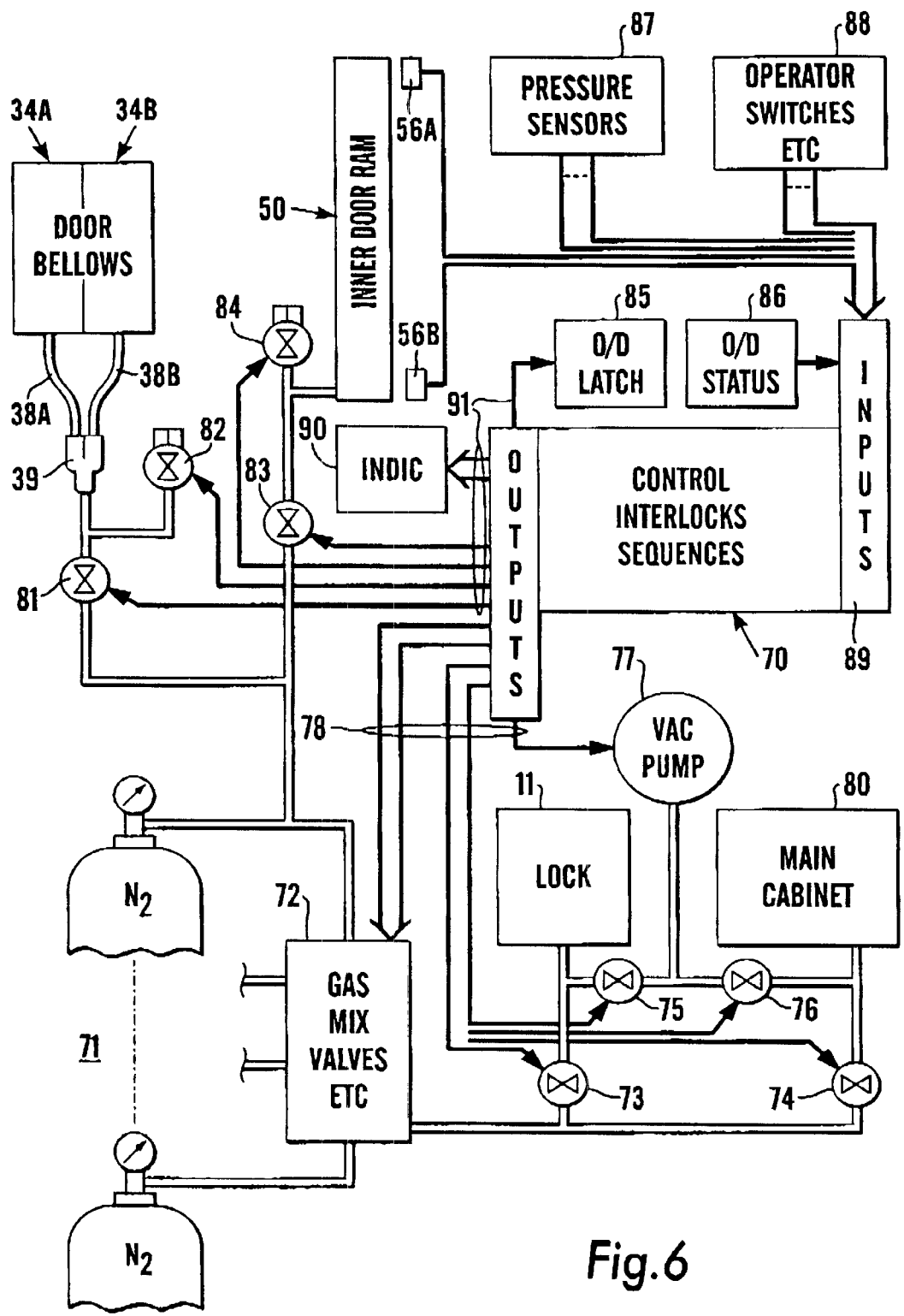

Specific implementation will now be indicated and described, by way of examples with reference to the accomanying diagramatic drawings, in which:

FIG. 1 is a perspective view of an access lock unit;
FIG. 2 is a front view showing some wall panel etc parts;
FIGS. 3A, B, C are internal plan and side and end views of a powered sealing sliding door;
FIGS. 4A, B are outline long and cross sectional views of a displacable door abutment;
FIGS. 5A, B are broken outline views of stackable tray provisions for aiding loading and unloading of sample stack,s and ancillary materials; and
FIGS. 6, 6A are block diagram of control provisions.

Lock unit cabinet 10 is shown generally cuboid with a lower access loading/unloading chamber 11 having related side connection provisions 12 for an adjacent atmosphere controlled cabinet (not shown) such as of anaerobic type (say as in our copending PCT application), and front opening outer door 13 indicated with bottom hinging 14 allowing opening downwards preferably to horizontal and level with floor of the chamber 11; and upper accommodation at 15 for control etc provisions under top cover 16 and behind conveniently forward-extending front control circuit/indicator/instrument panel provision 17. Side connection provisions 12 are shown extending outwards at 18 within optional attached trim 19 to flanging 21 with aperturing 22 and seal 23 for clamping sealed association with a similarly apertured wall of said adjacent cabinet. FIG. 2 omits some of front, top, side, etc panels that will be as readily affixed as indicated lower front panel 23A apertured for access via front door 13, and side panels 26A, B apertured for access through lock gide connection provisuis 12. The side puaels 26A, B form a hollow side wall construction within cavity 24 in which up-and-down sliding inner door 30 is operative.

The inner door 30 has a sheet 31 with spaced partition-iang 32A, B, C, D covered by another narrower sheet 33. At each side beyond other partitions 32A, D and other sheet 33, the sheet 31 carries a bellows device 34A, B shown with elongate extendable clamping bars 35A, B in resilient bellows diaphragms 36A, B and displaceable outwardly by pressurised gas applied via connections 37A, B through feed tubes 33A, B from a threeway connector 39 also fixed to the inner surface of the sheet 31. Such pressurised gas supply will extend the clamping bars 35A, B against inner surfaces of the side wall panel 26B about its aperturing. Sealing strip 40 about the outer surface of the sheet 31 adjacent its edges will then be compressed into sealing relation about the corresponding aperturing of the side wall panel 26A. Coiled gas supply tube 41 to the connector 39 comes from another connection 42 fixed through and extending from inner side wall of, cross-member or cover 43 conveniently with a seal 44 about step 45 to edge flanging 46 overfitting at or near top of the side wall cavity 24.

The cross-member or cover 43 also fixedly carries substantially centrally located cylinder 49 of pressurised gas operated ram 50 having its piston rod 51 attached at 52 inside the door 30. Pressurised gas supply to the ram 50 is to its cylinder 49 at Connector 53 through tube 54 from another connector 55 through the cross-member or cover 43. In addition, the cylinder 49 carries switches 56A, B at positions corresponding to opposite ends of its piston travel between open/up and closed/down positions of the door 30, respectively. Switches 56A, B are conveniently of magnetic reed type operated by a ferromagnetic piston or part, e.g. insert. Switch state signalling is via wire 57A, B and connectors 58A, B and 59.

It will be appreciated that the door 30 is wider and longer than access aperturing of cabinet side walls 26A, B and its sealing strip 40 will be outside such aperturing in the fully closed/down position of the door 30. Closing (lower) edge 30L of the door 30 thus needs to enter lower slot 24S, effectively part of the side wall cavity 24. Such entry is by displacement, advantageously fromn level with floor of the chamber 11 of a strip 60 shown spring-loaded against abutment ledges 62 by conical comression springs 61 preferably light-duty for ease of operation, and intended use, including tipping and twisting to remove for cleaning etc.

It is advantageous for the floor of the lock unit chamber 11 to be level not only with aperturing of the side-wall 26A, B but further with the associated main cabinet (see outline 80 in FIG. 6, and conveniently actually as in our copending PCT application), and for loading and unloading to be by way of trays 63 slidable over such floors. Then, it is further advantageous for such trays 63 to match in area inside their edge/locating walling 64 with an array of stacks of standard sample containers, typically so-called Petri dishes 65 for which stack-forming holders 66 of longitudinally-gapped (67) cylindrical structure are well known. A three-by-three such array is convenient, thus a generally rectangular tray 63, though advantageously with rounded corners to aid passing through quite closely matching with inner and outer access aperturing, i.e. the latter, even the floor area of the lock access chamber 11 needing to be only minimally over tray size, even height of holders 66. However, it is yet further advantageous for the trays 63 themselves to stack, especially in a mutual locating/retaining marner, see 63A, B in FIGS. 5A, B and particularly further with sufficient space in the lower tray 63B to accommodate materials and items of uae within the main cabinet, e.g swabs, tweezers etc etc. An arrangement including posts 68 and corner formations 69A, B it is viable to form between slow corners of the trays. 63 as desired above and curvature of normally circular sample dish and holder configurations.

Turning to preferred operation ot the lock unit 10, there will, of course, be suitable provision for all necessary and/or desired supply of pre-mixed gas or gases to be mixed, evacuating and flushing steps for achieving prescribed atmosphere establishment through appropriate valves and according to one or more effective cycles of operation. FIG. 6 gives general indication of such control etc provisions through such as a programmable logic controller 70, i.e. having PROM type program memory, configurable logic and processing facilities/capabilities, along with compressed gas supply cylinders 71, gas mixing valving etc 72 (typically including of variable selectable flow rate type), mixed gas supply valving 73, 74 to the lock chamber 11 and cabinet 80, evacuation valving 75, 76 therefrom to vaccuum pump 77, and control signal lines at 78.

FIG. 6 gives further specific indication of all of the inner door sealing bellows 34A, B and feeding tube/pipe further associated with electrically operated charging valve 81 and controlled rate release valve 82, say of adjustable rate venting needle type; the inner door raising ram 50 also along with similar charging and release valving 83, 84; and electrically operated locking/latching (85) and status indicating (86) provisions for the outer door 13. Nitrogen of customary atmosphere control gases is suitably inert for use in powered ram and bellows operation, see as indicated. Signal inputs from all of gas/atmosphere pressure sensors 87, operator inputs 88, the outer door status 86, and the inner door open/shut switches 56A, B are indicated at 89. Further control etc signal outputs for the valving B1–B3, the outer door latch 85 and indicators 90 are shown at 91.

Control features include advantageous interlocks and sequences relating at least to operating the inner door 30 using the switch 95 fron inside the associated main cabinet 80. Such opening will involve opening the valve 83 with the valve 84 closed to operate the ram 50, but only if the outer door is shut (86) and the atmosphere in the lock unit chamber 11 has been set up as prescribed, whereupon the sealing bellows devices 34A, B will be released by opening the valve 81 with the valve 82 closed. The outer door 13 will also be latched (85) closed until the inner door 30 is again closed (as indicated by the bottom reed switch 56B). If the inner door 30 does not fully open (as indicated by top reed switch SGB) within a predetermined time, the sealing bellows devices could operate automatically by reversing the states of the valves 81, 82 and/or closing operation of the door 30 initiated in absence of sensing of at least relevant gas pressure problems. Closing the inner door 30 by operating the switch 95 will involve closing the valve 63 and opening the venting valve 84, and can take place at a controlled rate simply by gravity action until bottom reed switch 56B operates after which bellows devices 34A, B will be charged by closing valve 82 and opening valve 81. Whilst the opening sequence for the inner door 30 conveniently continues after only momentary operation of the switch 95, which can conveniently be of push-action type, the closing sequence preferably requires continuous operation of the switch 95, and completion (bottom reed switch 56B) within a predetermined time, failing either of which states of the valves 83 and 84 will be automatically reversed and the inner door 30 driven open by the ram 50. The switch 95 is shown located so that its operation means an operator's hand cannot be under the door 30.

If the inner door 30 should begin to close without operation of the switch 95 (say sensed by top read switch 56A), as ay occur if there is a branch gas leak to the ram 50, the valves 82 and 83 will be closed and the valve 81 opened to energise the bellows devices 34A, B as an emergency braking measure. Another advantageous safety feature is available from sensing of any aberrant state, or specified condition, and closing all of the valves B1–B4 to "freeze" the state of equipment pending investigation and any necessary rectification. Such specified conditions preferably include drop of internal atmosphere gas pressure (normally at slight overpressure compared with outside ambient), and also such drop of operating gas pressure for the ram 50 and/or bellows devices 34A, B as still permits braking and sealing action by the bellows devices 34A, B. Indeed, mechanical rest-state bias of at least electrical valves B1–B4 may further secure such "freeze" state even for lose of electrical power.

It will be appreciated that preferred supply of operating gas compressed from a cylinder, particularly of inert atmosphere component gas, could be substituted by other gas and pressurising, say by way of electric motor or mains water driven turbine(s), even by pressurised liquid drive and/or of electrical, mechanical or electromechanical type (say motor-driven rack-and-pinion or lead-screw type).

For an anaerobic cabinet 80A using customary hydrogen, carbon dioxide and nitrogen gases, it is feasible to avoid any introduction of at least hydrogen into the lock unit 11, at least after first commissioning. Appropriate on-going anaerobic atmosphere control of typical cabinet 80A (see FIG. 6A) can be on a basis related to non-hydrogen gas flow thereto, say a pre-set volume of hydrogen being added for pre-set non-hydrogen gas flow, conveniently according to monitored nitrogen gas flow, say with carbon dioxide also at a pre-set rate of flow. In one example, a flow switch 101 permits such monitoring of nitrogen flow at the pre-set (101R) rate, say 55 litres per minute. For every pre-set time of such flow (see timer 102, but usually done within progratmable control logic), say 10 seconds, a hydrogen reservoir or accumulator 103 is charged to a pre-set pressure, say 1 bar (see exemplary piston 103P spring biassed 103S and limit switch 103L) for a 750 ml reservoir/accmulator volume, for automatic discharge (see limit switch operated valve 104) of such volume into the cabinet or workstation 80. Carbon dioxide flow rate is pre-set, say, at 5 litres per minute, and accompanies the nitrogen flow, see commonly controlled flow switch 105. Such gas flow provisions can be seen as variation on the gas mixing 72 of FIG. 6, but are indicated going direct to a gas manifold 106 of the workstation 80, as suits the further irdicated option of drawing of atmosphere for the lock unit 11 from the workstation so. Fully automatic commissioning cycle of about 45 minutes is then practical, see signal-controlled valves 107, 108, and levels of vaccuum drawn can be in the range of about 1–2.5 cm mercury. Preferably, either or both of commissioning and lock cycles are operator-terminable, and maximum over-pressure before vaccuum pump relief is about 10 cm water. Clearly, gas mixing can be dispensed with where a standard atmosphere is available economically in compressed gas cylinders and such is acceptable for pneumatic actuation.

What is claimed is:

1. Controlled atmosphere entry/exit lock unit for association with a controlled atmosphere cabinet, the lock unit having two controlled means for access, both operable alternatively for sealing and communicating, one relative to said cabinet and the other relative to outside, the lock unit further having means for atmosphere control operable for achieving internal atmosphere conditions compatible with what may be prescribed for said cabinet, the one controlled means for access having a movable door, and having means for sealing relative to access with said cabinet, and having related means for powered actuation of said door and of said means for sealing, operable to automatically coordinate opening and closing of the door with operation of the means for sealing.

2. Lock unit according to claim 1, comprising means for manual actuation of said means for powered actuation.

3. Lock unit according to claim 1, wherein the means for powered actuation includes means for inter-relating movement of the door only when said means for sealing is not actuated.

4. Lock unit according to claim 1, wherein the means for powered actuation includes means for inter-relating operation of said means for sealing when powering of the door is unavailable.

5. Lock unit according to claim 4, wherein operation of said means for sealing obstructs movement of the door.

6. Lock unit according to claim 1, wherein the one means for access is through a hollow wall having opposite faces between which a door component is slidably housed between positions closing or revealing registering access apertures through the opposite faces of the wall.

7. Lock unit according to claim 6, wherein the door has opposite faces one of which carries a resilient seal to circumscribe the aperture in the adjacent one of the faces of its wall, and the other of which carries means for expansion to engage the other face of the wall and clamp the door and compress the resilient seal.

8. Lock unit according to claim 7, wherein the wall has self-returning interior closure part at edge of the apertures, the closure part being displaceable by said door at closure of the apertures.

9. Lock unit according to claim 8 wherein the door is movable up and down.

10. Lock unit according to claim 9, wherein the closure part is contiguous with bottom of interior of the lock unit and said cabinet except when displaced.

11. Lock unit according to claim 1, wherein the means for powered actuation uses compressed gas.

12. Lock unit according to claim 11, wherein the door is movable up and down and the means for powered actuation includes a lifting ram for the door.

13. Lock unit according to claim 11, wherein the means for powered actuation includes bellows for said sealing.

14. Lock unit according to claim 12, comprising means for trapping and releasing compressed gas associated with the ram and/or bellows for said sealing.

15. Lock unit according to claim 14, wherein the compressed gas is of the atmosphere control means.

16. Lock unit according to claim 1, wherein the one means for access affords floor-engaging slide-through movement for carrier trays and contents between the lock unit and said cabinet.

17. Lock unit according to claim 16 in combination with carrier tray device, wherein said contents comprise an array of stack holders for sample containers.

18. Lock unit and carrier tray device according to claim 17, wherein another such tray device alone is stacked therewith and affords limited accommodation for items between the devices.

19. Lock unit according to claim 1, wherein the means for sealing is compression resilient.

* * * * *